United States Patent [19]

Moody

[11] 4,128,638
[45] Dec. 5, 1978

[54] NONA- AND DECA-PEPTIDE AMIDE DERIVATIVES DEMONSTRATING HIGH OVULATION INDUCING ACTIVITY

[75] Inventor: Keith Moody, Watsonia, Australia

[73] Assignee: ICI Australia Limited, Melbourne, Australia

[21] Appl. No.: 673,545

[22] Filed: Apr. 5, 1976

[30] Foreign Application Priority Data

Apr. 15, 1975 [AU] Australia ............................. PC1247

[51] Int. Cl.$^2$ ...................... A61K 37/02; C07C 103/52
[52] U.S. Cl. ............................. 424/177; 260/112.5 LH
[58] Field of Search ................. 260/112.5 LH; 424/177

[56] References Cited

U.S. PATENT DOCUMENTS

| 3,941,763 | 3/1976 | Sarantakis | 260/112.5 LH |
| 3,972,859 | 8/1976 | Fujino et al. | 260/112.5 LH |

FOREIGN PATENT DOCUMENTS 2183021  11/1972  France ........................... 260/112.5 LH

OTHER PUBLICATIONS

Ling, et al., Biochem. and Biophys. Res. Comm. 63, 1975, pp. 801–806.
Hirotsu, et al., Biochem. and Biophys. Res. Comm. 59, 1974, pp. 277–282.
Fujino, et al., Biochem. and Biophys. Res. Comm. 60, 1974, pp. 406–413.
White, Annual Reports in Medical Chemistry, vol. 8, 1973, pp. 204–213.
M. Fujino et al., Biochemical & Biophysical Research Comm., vol. 49, No. 3, 1972, pp. 698–705.

Primary Examiner—Delbert R. Phillips
Attorney, Agent, or Firm—Cushman, Darby & Cushman

[57] ABSTRACT

A peptide amide derivative of general formula (I) wherein when X is Gly, Y is Leu and Z is $\beta$-Ala-NH$_2$ or Sar-NH$_2$; when X is D-Ala, Y is Leu, Ile, Nle, Val, Nval, or Met and Z is Gly-NH$_2$, $\beta$-Ala-NH$_2$ or Sar-NH$_2$, provided that when X is D-Ala and Y is Leu Z is not Gly-NH$_2$; and when X is $\beta$-Ala, Y is Leu, Ile, Nle, Val, Nval or Met and Z is Gly-NH$_2$, $\beta$-Ala-NH$_2$, Sar-NH$_2$ or -NRR' wherein R and R', which may be the same or different, are H, lower alkyl containing from 1 to 6 carbon atoms, substituted lower alkyl containing from 1 to 6 carbon atoms, or together may form a ring; or a pharmaceutically acceptable acid-addition salt or metal-ion complex thereof; and an inert carrier therefor.

pGlu-His-Trp-Ser-Tyr-X-Y-Arg-Pro-Z        (I)

14 Claims, No Drawings

NONA- AND DECA-PEPTIDE AMIDE DERIVATIVES DEMONSTRATING HIGH OVULATION INDUCING ACTIVITY

This invention relates to nona- and decapeptide amide derivatives.

We have discovered novel nona- and decapeptide amide derivatives, which show high activity in releasing pituitary luteinizing hormone (LH) and follicle stimulating hormone (FSH), and as a consequence show high ovulation inducing activity.

Accordingly, we provide a peptide amide derivative of general formula (I) wherein when X is Gly, Y is Leu and Z is β-Ala-NH₂ or Sar-NH₂; when X is D-Ala, Y is Leu, Ile, Nle, Val, Nval or Met and Z is Gly-NH₂, β-Ala-NH₂ or Sar-NH₂, provided that when X is D-Ala and Y is Leu Z is not Gly-NH₂; and when X is β-Ala, Y is Leu, Ile, Nle, Val, Nval or Met and Z is Gly-NH₂, β-Ala-NH₂, Sar-NH₂ or -NRR' wherein R and R', which may be the same or different, are H, lower alkyl containing from 1 to 6 carbon atoms, substituted lower alkyl containing from 1 to 6 carbon atoms, or together may form a ring; or a pharmaceutically acceptable acid-addition salt or metal-ion complex thereof; and an inert carrier therefor.

pGlu-His-Trp-Ser-Tyr-X-Y-Arg-Pro-Z    (I)

Throughout this specification pGlu, His, Trp, Ser, Tyr, D-Ala, β-Ala, Leu, Ile, Nle, Val, Nval, Met, Arg, Pro, Gly and Sar represent "residues" of the amino acids L-pyroglutamic acid, L-histidine, L-tryptophan, L-serine, L-tyrosine, D-alanine, β-alanine, L-leucine, L-isoleucine, L-norleucine, L-valine, L-norvaline, L-methionine, L-arginine, L-proline, glycine and sarcosine respectively. By "residue" we refer to that portion of the amino acid lacking H from the amino group and OH from the carboxylic acid functionality, e.g. glycine has the structural formula, $H_2N\ CH_2CO_2H$, and so the glycine residue is the grouping, $-NH\ CH_2CO-$.

The hypothalamus is a gland in the brain which plays an important part in mammalian physiology. It has been known for some time that it gives rise to hormones that influence secretion from the anterior lobe of the pituitary gland of peptide hormones which control and regulate certain important bodily functions. The hypothalamic hormone of particular interest to the present invention is the luteinising hormone releasing hormone (LHRH) which acts on the pituitary gland to release the gonadotropin, luteinizing hormone (LH) and, to a lesser degree, it has also been shown to stimulate secretion of a second gonadotropin, follicle stimulating hormone (FSH). These two pituitary hormones are involved in controlling reproductive processes, the latter, FSH, acting on the ovaries to promote maturation of egg follicles, and the former, LH, to induce ovulation.

LHRH has been isolated from both ovine and porcine hypothalami and in each case has been shown to have the following decapeptide structure (2):

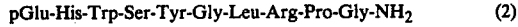

pGlu-His-Trp-Ser-Tyr-Gly-Leu-Arg-Pro-Gly-NH₂    (2)

(H. Matsuo, Y. Baba, R. M. G. Nair, A. Arimura, A. V. Schally, *Biochem. Biophys. Res. Comm*, 1971, 43(6), 1334; R. Burgus, M. Butcher, M. Amoss, N. Ling, M Monahan, J. Rivier, R. Fellows, R. Blackwell, W. Vale, R. Guillemin, *Proc. Nat. Acad. Sci (USA)*, 1972, 69, 278).

After the publication of these papers, several syntheses of the parent natural hormone and also of analogous compounds with similar amino acid sequence have been described. Results of biological testing on such synthetic analogues has shown that the integrity of sequence (2) is important for retaining high biological activity and it is important to note that even very minor structural modifications in such a large molecule can result in a large decrease in activity.

It is therefore surprising that the components of the present invention have high LH and FSH releasing activity. Some of these analogues in fact, show higher activity and also more prolonged activity than the natural decapeptide pGlu-His-Trp-Ser-Tyr-Gly-Leu-Arg-Pro-Gly-NH₂. The ovulation-inducing activity of some of these analogues is also higher. Such peptides have potential veterinary application for the purpose of animal breeding, e.g. in the treatment of seasonal and lactational anoestrous conditions, and also for use in conjunction with luteolytic agents for synchronization of oestrous.

The peptides described herein may be in the form of the free base or pharmaceutically acceptable acid-addition salts or metal complex salts thereof. Examples of pharmaceutically acceptable acid-addition salts are the hydrochloride, hydro-bromide, sulphate, phosphate, maleate, acetate, nitrate, benzoate, succinate, malate, ascorbate and the like. Examples of metal complex salts are those formed by reaction of an aqueous solution of the free base and a salt of metal such as zinc, nickel, cobalt, copper and iron.

The new compounds of our invention may be prepared by standard methods known to those skilled in the art. Preferably the new compounds are prepared by the solid phase procedure of Merrifield, (*JACS*, 1963, 85, 2149), or variants thereof, and preferably using a pellicular graft copolymer support. Alternatively, these peptides may also be made by classical solution synthesis.

The peptides are preferably synthesised on a pellicular solid phase support based on inert poly(chlorotrifluoroethylene) (PCTFE) onto which is grafted styrene to give approximately 4–8% polystyrene by weight.

The functional groups introduced into the aromatic rings of the grafted polystyrene, and used to anchor the growing peptide chain to the pellicular resin, are preferably the chloromethyl (Merrifield, *JACS*, 1963, 85, 2149) and benzhydrylamino groups (Pietta and Marshall, *Chem. Comm.* 1970, 650). The former is used in the synthesis of peptides with N-alkyl substituted carboxamide terminus and the latter for those with a primary carboxamide terminus.

The synthesis is begun at the carboxyl terminus, and the first amino acid residue is attached to the chloromethyl resin in a nucleophilic displacement of the benzylic chlorine by a carboxylate salt of the appropriate amino acid. Use of several methods and various salts has been described in the published literature but the one of choice uses the caesium salt in dimethylformamide (DMF) (Gisin, *Helv. Chim. Acta*, 1973, 56, 1476). In this and subsequent coupling reactions, the α-amino substituent is protected by the tert-butyloxycarbonyl substituent (BOC), except in the case of pyroglutamic acid which is used as such. Arginine is also used with tert-amyloxycarbonyl (AOC) protection off the α-amino group. Side chain protecting groups are used with those amino acids having functional groups in the side chain otherwise capable of reacting during coupling reactions, e.g. histidine as the $N^{im}$-tosyl derivative; serine, O-benzyl; tyrosine, O-2,6-dichlorobenzyl; and arginine, $N^G$-tosyl. The BOC (or AOC) protecting groups are removed by treatment with 30% trifluoroacetic acid in methylene chloride and the resultant ammonium salt neutralized with 10% triethylamine in methylene chloride. The method of choice for addition of further suitably-protected amino acids is a carbodiimide-mediated coupling, although a number of other methods could be used. α-amino deprotection and neutralization steps precede each coupling. In using the benzhydrylamine resin to synthesise peptides with a primary carboxamide terminus, the first coupling step (as well as subsequent couplings) is mediated preferably by carbodiimide.

Peptide sequences assembled on the chloromethyl resins are cleaved from the resin by cleavage of the ester anchor bond with an appropriate amine to give a side chain-protected peptide with a N-substituted carboxamide terminus. Side chain deprotection is accomplished with hydrogen fluoride in the presence of anisole.

Hydrogen fluoride treatment of the benzhydrylamine peptide-resins results in cleavage from the resin and side chain deprotection in one step to give peptides with a primary carboxamide terminus. Such peptides may also be obtained by assembly of the same sequence on a chloromethyl resin followed by cleavage with ammonia and side chain deprotection with hydrogen fluoride. The solid phase procedure for synthesis of the described peptides may, however, be carried out in a variety of ways employing various combinations of the functional group or the solid support, the α-amino and side chain protecting groups, the coupling reagent, and the cleavage and deprotecting reagent.

The invention is now illustrated by, but by no means limited to, the following examples.

EXAMPLE 1

L-Pyroglutamyl-L-histidyl-L-tryptophanyl-L-seryl-L-tyrosyl-β-alanyl-L-leucyl-L-arginyl-L-prolyl-glycinamide. (β-Ala$^6$-LHRH)

The solid support, a PCTFE-g-benzhydrylaminostyrene resin (5.556g) of mesh size 100-200 BSS, containing 6.7% w/w grafted styrene, and substituted by benzhydrylamino groups to the extent of 0.09 mmole/g (total reactive amine content, 0.5 mmole), was preswollen in methylene chloride (20 ml) for 30 minutes in a reaction vessel fitted with a sintered glass filter disc and rotated about a longitudinal axis. After filtering, the resin was treated with BOC-glycine (219 mg, 1.25 mmole) in methylene chloride (20 ml) for 10 min before adding 50% (w/v) dicyclohexylcarbodiimide/methylene chloride (0.52 ml, 1.25 mmole). The success of this and subsequent couplings was monitored by the ninhydrin reaction as described by Kaiser (et al), *Anal. Biochem.*, 1970, 34, 595; in most cases coupling was complete within one hour.

After filtering, the resin was treated as follows: (1) Washed 5X methylene chloride (20 ml) (3 min/wash). (2) The BOC protecting group was removed by treating twice with 30% trifluoroacetic acid/methylene chloride (20 ml) (pretreatment for 5 min and a second 30 min treatment). (3) Washed 5X methylene chloride (20 ml) (3 min/wash). (4) The trifluoroacetic salt of the amino terminus was neutralized in two treatments with 10% triethylamine/methylene chloride (20 ml) (pretreatment for 5 min and a second 15 min treatment). (5) Washed 5X methylene chloride (20 ml) (3 min/wash).

This procedure was repeated to assemble the required amino acid sequence. Further couplings used the appropriately protected amino acid (1.25 mmoles) and dicyclohexylcarbodiimide (1.25 mmole) usually in methylene chloride (15 ml), except with L-pyroglutamic acid where dimethylformamide/methylene chloride (1:1 v/v) was used, and in the case of BOC-L-tryptophan and BOC-$N^G$-tosyl-L-arginine where a small amount of dimethylformamide was added to methylene chloride to effect solution. On deprotection following introduction of L-tryptophan, 1% (v/v) 2-mercaptoethanol was added to the methylene chloride in steps (2) and (3) above.

After coupling L-pyroglutamic acid, the peptide-resin was filtered, washed 3X dimethylformamide (20 ml) and 3X methylene chloride (20 ml), dried, and then cleaved and deprotected by treatment at 0° C. for 1 hour with hydrogen fluoride (10 ml)/anisole (2.5 ml). Hydrogen fluoride and anisole were evaporated in vacuo, the resin dried over sodium hydroxide to remove final traces of acid, and then extracted with ether (4 × 30 ml) to remove traces of anisole. Extraction (4X) of the resin with 1M AcOH (30 ml) yielded crude peptide (387 mg), which was purified by (a) ion exchange chromatography on carboxymethylcellulose with 0.1 M ammonium acetate (b) gel permeation chromatography on Biogel P2 L with 1M acetic acid, and (c) partition chromatography on Sephadex G-25 with n-butanol: acetic acid: water = 4:1:5 (Yamashiro, *Nature*, 1964, 201, 76) to give β-Ala$^6$-LHRH (138 mg).

$R_f1$, 0.17; $R_f2$, 0.35, wherein here and below 1 and 2 refer to the solvent systems chloroform: methanol: IM acetic acid = 60:45:20 (bottom phase), and n-butanol: acetic acid: water = 4:1:5 (top phase) respectively, used in conjunction with silica gel t.l.c. plates (0.3 mm thickness and air-dried) containing a fluorescent indicator. For comparison luteinizing hormone releasing hormone (LHRH) had $R_f1$ 0.18 and $R_f2$ 0.36 in these solvent systems. Both this peptide and others described below were homogeneous in these t.l.c. systems when visualized by ultraviolet light (254 nm), and with Ehrlich and chlorine peptide sprays (J. M. Stewart, J. D. Young, "Solid Phase Peptide Synthesis" pp 62-3 (W. H. Freeman: San Francisco 1969).

Amino acid analysis (hydrolysis with 6N HCl/22hr/110° C.): Glu, 1.08; His, 1.18; Ser, 0.92; Tyr, 0.95; Leu, 1.02; Arg, 0.93; Pro, 1.05; Gly, 1.06; Trp and β-Ala were present.

EXAMPLE 2

L-Pyroglutamyl-L-histidyl-L-tryptophanyl-L-seryl-L-tyrosylglycyl-L-leucyl-L-arginyl-L-prolyl-β-alaninamide. (β-Ala$^{10}$-LHRH)

β-Ala$^{10}$-LHRH was synthesised and purified by an analogous method to that described above in Example 1 using the same PCTFE-g-benzhdrylaminostyrene resin (total reactive amine content, 0.5 mmole). Yield of purified peptide, 98 mg. $R_f1$, 0.18; $R_f2$, 0.35. (LHRH: $R_f1$, 0.18; $R_f2$, 0.36).

Amino acid analysis (hydrolysis with 6 N HCl/22 hr/110° C.): Glu, 1.08; His, 1.06; Ser, 0.94; Tyr, 0.88; Gly, 1.05, Leu, 1.01; Arg, 0.94; Pro, 1.05; β-Ala and Trp were present.

EXAMPLE 3

L-Pyroglutamyl-L-histidyl-L-tryptophanyl-L-seryl-L-tyrosylglycyl-L-leucyl-L-arginyl-L-prolysarcosinamide. (Sar$^{10}$-LHRH).

Sar$^{10}$-LHRH was synthesised and purified by an analogous method to that described in Example 1 using the same PCTFE-g-benzhydrylamino resin (total reactive amine content, 0.5 mmole). Yield of purified peptide, 48 mg. $R_f1$, 0.20; $R_f2$, 0.34. (LHRH: $R_f1$, 0.18; $R_f2$, 0.36). Amino acid analysis (hydrolysis with 6N HCl/22hr/110° C.): Glu, 1.06; His, 0.96; Ser, 0.92; Tyr, 0.98; Gly, 1.05; Leu, 1.01; Arg, 1.01; Pro, 1.01; Sar was present.

EXAMPLE 4

L-Pyroglutamyl-L-histidyl-L-tryptophanyl-L-seryl-L-tyrosyl-D-alanyl-L-isoleucyl-L-arginyl-L-prolyl-glycinamide (D-Ala$^6$-Ile$^7$-LHRH) and
L-pyroglutamyl-L-histidyl-L-tryptophanyl-L-seryl-L-tyrosyl-D-alanyl-L-valyl-L-arginyl-L-prolylglycinamide (D-Ala$^6$-Val$^7$-LHRH).

D-Ala$^6$-Ile$^7$-LHRH and D-Ala$^6$-Val$^7$-LHRH were prepared in parallel using the same PCTFE-g-benzhydryl-aminostyrene resin (16.39 g) of mesh size 100-150BSS, containing 5.5% w/w grafted polystyrene, and substituted by benzhydrylamino groups to the extent of 0.061 mmole/g (total reactive amine content = 1.0 mmole). A synthesis analogous to that described in Example 1 was used involving the repetitive coupling, deprotection and neutralization procedure with the appropriate BOC-amino acid (N$^G$-tosyl-AOC-arginine was used in this synthesis). After the addition of the first three amino acid residues, viz glycine, proline and arginine, the total quantity of peptide-resin was halved. To one half BOC-isoleucine was coupled and the remaining residues then added to give D-Ala$^6$-Ile$^7$-LHRH peptide-resin. To the other BOC-valine was coupled and assembly of the remaining part of the sequence was completed to give D-Ala$^6$-Val$^7$-LHRH peptide-resin.

The two peptide-resins were separately cleaved and deprotected with hydrogen fluoride as outlined in Example 1 to give crude D-Ala$^6$-Ile$^7$-LHRH (475 mg) and crude D-Ala$^6$-Val$^7$-LHRH (495 mg).

D-Ala$^6$-Ile$^7$-LHRH (89 mg) was obtained from purification of crude peptide by (a) ion exchange chromatography on carboxymethylcellulose with 0.1M ammonium acetate (b) chromatography on silica gel with chloroform/methanol/IM acetic acid = 60:45:20 (bottom phase); and (c) gel permeation chromatography on Biogel P2 with IM acetic acid. $R_f1$, 0.19; $R_f2$, 0.30 (LHRH): $R_f1$, 0.17; $R_f2$, 0.29).

D-Ala$^6$-Val$^7$-LHRH (146 mg) was obtained by the same purification system outlined above. $R_f1$, 0.11; $R_f2$, 0.28 (LHRH): $R_f1$, 0.17; $R_f2$, 0.29).

EXAMPLE 5

L-Pyroglutamyl-L-histidyl-L-tryptophanyl-L-seryl-L-tyrosyl-$\beta$-alanyl-L-leucyl-L-arginyl-L-prolinamide.
($\beta$-Ala$^6$-des-Gly$^{10}$-LHRH).

$\beta$-Ala$^6$-des-Gly$^{10}$-LHRH was synthesized, by an analogous procedure to that outlined in Example 1 using PCTFE-g-benzhydrylaminostyrene resin (7.54 g) of mesh size 150-200 BBS, containing 5.6% w/w grafted polystyrene, and substituted by benzhydrylamino groups to the extent of 0.065 mmole/g (total reactive amine content = 0.5 mmole). N$^G$-Tosyl-AOC-arginine was the arginine derivative used in this synthesis.

The crude peptide (590mg) was purified by the chromatographic procedure described in Example 4 to give $\beta$-Ala$^6$-des-Gly$^{10}$-LHRH (51 mg). $R_f1$, 0.20; $R_f2$, 0.35; (LHRH: $R_f1$, 0.18; $R_f2$, 0.36).

Amino acid analysis (hydrolysis with 6N HCl/22 hr/110° C.): Glu, 1.00; His, 0.83; Ser, 0.85; Tyr, 0.87; $\beta$-Ala, 1.07, Leu, 0.96; Arg, 0.99; Pro, 0.98; Trp was present.

EXAMPLE 6

L-Pyroglutamyl-L-histidyl-L-tryptophanyl-L-seryl-L-tyrosyl-$\beta$-alanyl-L-leucyl-L-arginyl-L-proline
N-methylamide ($\beta$-Ala$^6$-des-Gly$^{10}$-LHRH methylamide).

The solid support, a PCTFE-g-chloromethylstyrene resin (23.88 g), of mesh size 100-150 BSS, containing 6.9% w/w grafted styrene, and substituted with chloromethyl groups to the extent of 0.134 mmole/g (total chloromethyl content, 3.2 mmole) was reacted with BOC-L-proline caesium salt (prepared as described by Gisin, *Helv. Chim. Acta*, 1973, 56, 1476) (4.8 mmoles) in dimethylformamide (50 ml) at 51° C. for 24 hr. The resin was filtered and washed with dimethylformamide (XI), dimethylformamide: water (9:1) (X3), dimethylformamide (X1), ethanol (X3) and methylene chloride (X3). Deprotection and neutralization were carried out as described in steps (2)–(5) in Example 1. To complete assembly of the remaining part of the sequence, the repetitive coupling, deprotection and neutralization procedure outlined in Example 1 was used. Coupling steps employed dicyclohexylcarbodiimide (8.0 mmoles) and the BOC - protected amino acid (8.0 mmoles); in the case of arginine α-AOC protection was used.

One-eighth of the resultant peptide-resin was treated with 33% methylamine in ethanol (20 ml) for 65 hr at room temperature. Filtration and evaporation gave side-chain - protected peptide (419mg). Two more treatments of the resin with ethanolic methylamine gave a further 20 mg of peptide. The combined product was deprotected with hydrogen fluoride/anisole as described in Example 1 and then purified by chromatography as outlined in Example 4 to give $\beta$-Ala$^6$-des-Gly$^{10}$-LHRH methylamide (47 mg). $R_f1$, 0.27; $R_f2$, 0.37 (LHRH: $R_f1$, 0.18; $R_f2$, 0.36).

Amino acid analysis (hydrolysis with 6N HCl/22 hr/110° C.): Glu, 1.07; His, 0.76; Ser, 0.91; Tyr, 0.93; $\beta$-Ala, 1.08; Leu, 0.89; Arg, 1.07; Pro, 1.05.

EXAMPLE 7

L-Pyroglutamyl-L-histidyl-L-tryptophanyl-L-seryl-L-tyrosyl-$\beta$-alanyl-L-leucyl-L-arginyl-L-proline
N-ethylamide ($\beta$-Ala$^6$-des-Gly$^{10}$-LHRH ethylamide).

One-eighth of the peptide-resin obtained in Example 6 was treated with ethylamine (20 ml) at 5° C. for 23 hr to yield crude side chain-protected ethylamide (385 mg); a further 34 mg of peptide was obtained from a second treatment of the resin with ethylamine. Combined product was processed as described for the corresponding methylamide in Example 6 to give $\beta$-Ala$^6$-des-Gly$^{10}$-LHRH ethylamide (57 mg). $R_f1$, 0.29; $R_f2$, 0.38; (LHRH: $R_f1$, 0.18; $R_f2$, 0.36).

Amino acid analysis (hydrolysis with 6N HCl/22hr/110° C.): Glu, 1.05; His, 1.00; Ser, 0.88; Tyr, 0.96; β-Ala, 1.25; Leu, 1.03; Arg, 1.05; Pro, 1.03; Trp was present.

EXAMPLE 8

L-pyroglutamyl-L-histidyl-L-tryptophanyl-L-seryl-L-tyrosyl-β-alanyl-L-leucyl-L-arginyl-L-proline N-n-propylamide (β-Ala$^6$-des-Gly$^{10}$-LHRH n-propylamide).

One-eighth of the peptide-resin obtained in Example 6 was treated with n-propylamine (20 ml) for 65 hr at room temperature to yield crude side chain-protected n-propylamide (501 mg); two more treatments afforded a further 48 mg. Combined product was processed as described for the corresponding methylamide in Example 6 to give β-Ala$^6$-des-Gly$^{10}$-LHRH n-propylamide (61 mg). $R_f1$, 0.33; $R_f2$, 0.40 (LHRH: $R_f1$, 0.18; $R_f2$, 0.36).

Amino acid analysis (hydrolysis with 6N HCl/22 hr/110° C.): Glu, 1.03; His, 0.97; Ser, 0.89; Tyr, 0.56; Leu, 1.01; Arg, 0.96; Pro, 1.02; Trp was present.

EXAMPLE 9

L-Pyroglutamyl-L-histidyl-L-tryptophanyl-L-seryl-L-tyrosyl-β-alanyl-L-leucyl-L-arginyl-L-proline pyrrolidide (β-Ala$^6$-des-Gly$^{10}$-LHRH pyrrolidide).

One-eighth of the peptide-resin obtained in Example 6 was treated with pyrrolidine (20 ml) for 24 hr at room temperature to yield the side-chain protected pyrrolidide (193 mg); two subsequent treatments of the resin with pyrrolidine (10 ml) for 64 to 24 hr to yielded 218 and 63 mg of pyrrolidide respectively. Combined product was processed as described for the corresponding methylamide in Example 6 to give β-Ala$^6$-des-Gly$^{10}$-LHRH pyrrolidide (19 mg). $R_f1$, 0.34; $R_f2$, 0.37 (LHRH: $R_f1$, 0.18; $R_f2$, 0.36).

Amino acid analysis (hydrolysis with 6N HCl/22 hr/110° C.): Glu, 1.06; His, 0.96; Ser, 0.90; Tyr, 1.01; β-Ala, 1.33; Leu, 1.02; Arg, 1.04; Pro, 1.02.

EXAMPLE 10

Bioassay for LH release by the synthetic peptides described in this invention

The table below shows details of bioassay results for each of the peptides of Examples 1–3 in respect of their ability to release LH from the pituitary gland of ovariectomized ewes at two different dose levels.

Each ewe was bled twice by jugular venipuncture before administration of the analogue, to establish basal levels of LH in plasma. Following intravenous injection of the appropriate analogue dissolved in saline solution (1 ml), blood samples were collected at intervals over the next three hours, centrifuged and subjected to radio-immunoassay for LH.

| Example No. | LHRH Analogue | Dose (μg) | P* |
|---|---|---|---|
| 1 | β-Ala$^6$-LHRH | 25 | 108 |
|   |   | 2.5 | 97 |
| 2 | β-Ala$^{10}$-LHRH | 50 | 75 |
|   |   | 5 | 12 |
| 3 | Sar$^{10}$-LHRH | 50 | 45 |
|   |   | 5 | 70 |

P* is the maximal release of LH by the LHRH analogue at a given dose expressed as a percentage of the LH release by LHRH at the same dose.

EXAMPLE 11

Ovulation-inducing ability of the synthetic peptides described in this invention The synthetic LHRH analogues described above have been found to induce ovulation in androgen-sterilized, constant-oestrous rats, in some cases to good effect at very low levels. This activity is exemplified in the table below:

| LHRH Analogue | Intravenous dose/rat | Ovulating rats/group |
|---|---|---|
| D-Ala$^6$-Ile$^7$-LHRH | 0.25 μg | 3/3 |
| D-Ala$^6$-Val$^7$-LHRH | 0.25 μg | 3/3 |
| β-Ala$^6$-des-Gly$^{10}$-LHRH methylamide | 0.25 μg | 3/3 |
| β-Ala$^6$-des-Gly$^{10}$-FHRH ethylamide | 0.25 μg | 3/3 |
| β-Ala$^6$-des-Gly$^{10}$-LHRH n-propylamide | 0.25 μg | 5/6 |
| β-Ala$^6$-des-Gly$^{10}$-LHRH pyrrolidide | 0.25 μg | 3/3 |

I claim:

1. A peptide amide derivative selected from the group consisting of:
L-pyroglutamyl-L-histidyl-L-tryptophanyl-L-seryl-L-tyrosyl-β-alanyl-L-leucyl-L-arginyl-L-prolyl-glycinamide;
L-pyroglutamyl-L-histidyl-L-tryptophanyl-L-seryl-L-tyrosyl-glycyl-L-leucyl-L-arginyl-L-prolyl--alaninamide;
L-pyroglutamyl-L-histidyl-L-tryptophanyl-L-seryl-L-tyrosyl-glycyl-L-leucyl-L-arginyl-L-prolyl-sarcosinamide;
L-pyroglutamyl-L-histidyl-L-tryptophanyl-L-seryl-L-tyrosyl-β-alanyl-L-leucyl-L-arginyl-L-proline N-methylamide;
L-pyroglutamyl-L-histidyl-L-tryptophanyl-L-seryl-L-tyrosyl-β-alanyl-L-leucyl-L-arginyl-L-proline N-ethylamide;
L-pyroglutamyl-L-histidyl-L-tryptophanyl-L-seryl-L-tyrosyl-β-alanyl-L-leucyl-L-arginyl-L-proline N-n-propylamide;
and L-pyroglutamyl-L-histidyl-L-tryptophanyl-L-seryl-L-tyrosyl-β-alanyl-L-leucyl-L-arginyl-L-proline pyrrolidide.

2. The peptide amide L-pyroglutamyl-L-histidyl-L-tryptophanyl-L-seryl-L-tyrosyl-β-alanyl-L-leucyl-L-arginyl-L-prolyl-glycinamide. (β-Ala$^6$-LHRH).

3. The peptide amide L-pyroglutamyl-L-histidyl-L-tryptophanyl-L-seryl-L-tyrosyl-glycyl-L-leucyl-L-arginyl-L-prolyl-β-alaninamide. (β-Ala$^{10}$-LHRH).

4. The peptide amide L-pyroglutamyl-L-histidyl-L-tryptophanyl-L-seryl-L-tyrosyl-glycyl-L-leucyl-L-arginyl-L-prolyl-sarcosinamide. (Sar$^{10}$-LHRH).

5. The peptide amide L-pyroglutamyl-L-histidyl-L-tryptophanyl-L-seryl-L-tyrosyl-β-alanyl-L-leucyl-L-arginyl-L-proline N-methylamide. (β-Ala$^6$-des-Gly$^{10}$-LHRH methylamide).

6. The peptide amide L-pyroglutamyl-L-histidyl-L-tryptophanyl-L-seryl-L-tyrosyl-β-alanyl-L-leucyl-L-arginyl-L-proline N-ethylamide. (β-Ala$^6$-des-Gly$^{10}$-LHRH ethylamide).

7. The peptide amide L-pyroglutamyl-L-histidyl-L-tryptophanyl-L-seryl-L-tyrosyl-β-alanyl-L-leucyl-L-arginyl-L-proline N-n-propylamide. (β-Ala$^6$-des-Gly$^{10}$-LHRH n-propylamide).

8. The peptide amide L-pyroglutamyl-L-histidyl-L-tryptophanyl-L-seryl-L-tyrosyl-β-alanyl-L-leucyl-L- arginyl-L-proline pyrrolidide. ($\beta$-Ala$^6$-des-Gly$^{10}$-LHRH-pyrrolidide).

9. A composition of matter for the treatment of mammals to induce ovulation comprising an effective amount of a peptide amide derivative selected from the group consisting of:

L-pyroglutamyl-L-histidyl-L-tryptophanyl-L-seryl-L-tyrosyl-$\beta$-alanyl-L-leucyl-L-arginyl-L-prolyl-glycinamide;

L-pyroglutamyl-L-histidyl-L-tryptophanyl-L-seryl-L-tyrosyl-glycyl-L-leucyl-L-arginyl-L-prolyl-$\beta$-alaninamide;

L-pyroglutamyl-L-histidyl-L-tryptophanyl-L-seryl-L-tyrosyl-glycyl-L-leucyl-L-arginyl-L-prolyl-sarcosinamide;

L-pyroglutamyl-L-histidyl-L-tryptophanyl-L-seryl-L-tyrosyl-$\beta$-alanyl-L-leucyl-L-arginyl-L-proline N-methylamide;

L-pyroglutamyl-L-histidyl-L-tryptophanyl-L-seryl-L-tyrosyl-$\beta$-alanyl-L-leucyl-L-arginyl-L-proline N-ethylamide;

L-pyroglutamyl-L-histidyl-L-tryptophanyl-L-seryl-L-tyrosyl-$\beta$-alanyl-L-leucyl-L-arginyl-L-proline N-n-propylamide;

and L-pyroglutamyl-L-histidyl-L-tryptophanyl-L-seryl-L-tyrosyl-$\beta$-alanyl-L-leucyl-L-arginyl-L-proline pyrrolidide and an inert carrier therefor.

10. A composition according to claim 1 suitable for administration by injection comprising a sterile saline solution of said peptide amide derivative.

11. A method of treating mammals to promote maturation of egg follicles and induce ovulation by administering to the mammal a therapeutic dose of a composition according to claim 1.

12. A method according to claim 11 wherein the composition is administered in a single dose.

13. A method according to claim 11 wherein the composition is administered by infusion.

14. A method according to claim 11 wherein the composition is administered by intravenous injection.

* * * * *